United States Patent
Tarinelli et al.

(10) Patent No.: US 8,261,907 B2
(45) Date of Patent: Sep. 11, 2012

(54) WOUND CLOSURE ADHESIVE REMOVER

(75) Inventors: Danyel J. Tarinelli, Middletown, CT (US); Ahmad R. Hadba, Wallingford, CT (US); Nadya Belcheva, Middletown, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 452 days.

(21) Appl. No.: 12/298,611

(22) PCT Filed: Jun. 29, 2007

(86) PCT No.: PCT/US2007/015094
§ 371 (c)(1),
(2), (4) Date: Oct. 27, 2008

(87) PCT Pub. No.: WO2008/005314
PCT Pub. Date: Jan. 10, 2008

(65) Prior Publication Data
US 2009/0118658 A1    May 7, 2009

Related U.S. Application Data

(60) Provisional application No. 60/817,675, filed on Jun. 30, 2006.

(51) Int. Cl.
*B65D 81/24* (2006.01)
(52) U.S. Cl. ............... 206/210; 206/209; 206/227
(58) Field of Classification Search ........... 206/209, 206/210, 361, 362, 362.1, 362.2, 362.3, 229
See application file for complete search history.

(56) References Cited

U.S. PATENT DOCUMENTS

| | | | | |
|---|---|---|---|---|
| 3,759,375 | A * | 9/1973 | Nappi | 206/362 |
| 4,321,257 | A * | 3/1982 | Sipos | 424/78.06 |
| 4,887,994 | A * | 12/1989 | Bedford | 604/1 |
| 4,900,721 | A * | 2/1990 | Bansemir et al. | 514/25 |
| 4,952,204 | A * | 8/1990 | Korteweg | 604/1 |
| 5,017,617 | A * | 5/1991 | Kihara et al. | 514/635 |
| 5,240,415 | A * | 8/1993 | Haynie | 433/216 |
| 5,368,581 | A * | 11/1994 | Smith et al. | 604/290 |
| 5,846,215 | A * | 12/1998 | Zygmont | 604/1 |
| 5,947,986 | A * | 9/1999 | Lewis | 606/161 |
| 6,364,101 | B1 * | 4/2002 | Schultz | 206/210 |
| 6,372,313 | B1 * | 4/2002 | D'Alessio et al. | 428/34.1 |
| 6,387,068 | B1 * | 5/2002 | Naughton | 604/2 |
| 6,405,735 | B1 * | 6/2002 | Dockery | 132/74.5 |
| 6,592,860 | B1 | 7/2003 | Levy et al. | |
| 6,802,416 | B1 * | 10/2004 | D'Alessio et al. | 206/229 |
| 6,936,268 | B1 * | 8/2005 | Muta et al. | 424/402 |
| 6,998,510 | B2 | 2/2006 | Buckman et al. | |
| 7,030,077 | B2 * | 4/2006 | Beers et al. | 510/344 |

(Continued)

OTHER PUBLICATIONS

International Search Report for PCT/US07/015094 date of completion is Feb. 29, 2008 (9 pages).

*Primary Examiner* — David Fidei

(57) ABSTRACT

A kit for storing and applying an adhesive removing device comprising an enclosure which includes a base portion and a removable top layer releasably secured to the base portion; an adhesive removing device including at least one wiping mechanism which includes at least one absorbent portion; and a biocompatible composition including a solvent and a moisturizing agent embedded in the absorbent portion of the wiping mechanism. A method for storing and applying an adhesive removing device comprises a series of steps for using the adhesive removing device to remove an adhesive from a surface.

22 Claims, 2 Drawing Sheets

U.S. PATENT DOCUMENTS

2005/0092624 A1* 5/2005 Harper .................... 206/205
2005/0271692 A1* 12/2005 Gervasio-Nugent et al. . 424/401
2005/0281776 A1* 12/2005 Courcoux et al. ............. 424/74
2006/0147397 A1* 7/2006 Uehara et al. .................. 424/62
2007/0166251 A1* 7/2007 Dayan et al. ................... 424/62
2007/0269392 A1* 11/2007 Sunkara ......................... 424/59
2007/0275021 A1* 11/2007 Lee et al. ..................... 424/401

* cited by examiner

WOUND CLOSURE ADHESIVE REMOVER

CROSS-REFERENCE TO RELATED APPLICATIONS

This application is a National State Application of PCT/US2007/015094 filed Jun. 29, 2007 under 35 USC §371(a), which claims priority of U.S. Provisional Patent Application Ser. No. 60/817,675 filed Jun. 30, 2006, the disclosures of each of the above-identified applications are hereby incorporated by reference in their entirety.

BACKGROUND

1. Technical Field

The present disclosure relates generally to devices for removing adhesive and to packaging for storing and dispensing such devices, and more particularly to devices and methods for removing wound closure topical adhesives.

2. Background of Related Art

Biocompatible solvent compositions are known to be used on adhesive articles in order to solubilize the adhesive used in wound closure. For example, it is known to apply a biocompatible solvent composition such as isopropyl alcohol to an adhesive such as cyanoacrylate by various methods such as by spray applicator, a sponge applicator, or a towelette applicator. However, these methods have proved to be inconvenient, time consuming and unsuccessful particularly in difficult to reach or isolated environments.

Illustratively, it is difficult to apply compositions with low viscosity using conventional devices. If the low viscosity composition is stored in a container, the user will squeeze the container to dispense a quantity of the composition. However, it is difficult to squeeze the container such that the correct amount of the composition is dispensed. It is often the case that the container is squeezed too much and a large quantity of the composition is dispensed. As a result, the composition may flow into areas to which the user did not intend to apply the composition. This results in increased time to effect the removal of the adhesives as well as waste of the solvent product.

An alternative approach to applying a solvent composition is to initially apply the solvent from a storage container onto an applicator and then onto the target surface. In such an approach, a user squeezes the container, for example, containing the solvent composition so as to apply a portion of the solvent onto the applicator. The applicator is then moved into physical contact with the adhesive so that the adhesive would be solubilized. However, solvents with low viscosity compositions may run off the applicator before it is adjacent the surface.

If the solvent composition is stored in a bottle, the user inverts the bottle to dispense a quantity of the solvent onto an applicator such as a swab, towelette or sponge applicator. However, inverting a bottle of solvent composition frequently and unpredictably results in dispensing more solvent than is necessary and increases the chances of contaminants to be transferred into the bottle and on the applicator.

Further, a problem arises if the container of solvent composition is to be used more than once, as is common. If a user chooses to apply the solvent composition directly from the container onto the surface, and not to use an applicator, the dispensing tip may contact the surface upon which the solvent is being applied. Over multiple uses, contaminants may be transferred from one surface to another surface. As is apparent, this is especially of concern with the application of compositions in the medical field.

Further, there are other problems associated with conventional techniques with the application of solvent compositions in certain environments, particularly ones in which the surface is difficult to reach or is isolated. If a user wishes not to use an applicator, it is necessary for the dispensing tip of the container to be positioned adjacent to or on the surface. However, the container may not easily fit within the spatial constraints in which the surface is located. As a result, the spatial constraints may limit applications using only the container and force a user to use an applicator. This raises a further problem in that an appropriate applicator may not be conveniently available.

Conventional devices fail to provide an applicator and/or a kit that is optimized for convenient dispensing and application of biocompatible solvent materials for removal of adhesives on a variety of surfaces and structures.

SUMMARY

Accordingly, an adhesive removing device in accordance with the present disclosure to address the need for an easy to use and efficient package assembly for dispensing and applying an adhesive remover, preferably for wound closure adhesives.

In one embodiment, the package assembly includes a sterilized enclosure containing a wiping mechanism or applicator with a biocompatible composition embedded in the absorbent portion of a wiping mechanism or applicator, for applying to and removing adhesives. The biocompatible composition includes a solvent and moisturizing agent. The solvent includes, but is not limited to isopropyl alcohol, benzyl alcohol, esters of acetic acid and/or mixtures thereof. The moisturizing agent includes but is not limited to aloe. In some embodiments, the absorbent portion of the applicator is wrapped with a removable plastic layer.

The disclosure provides an easy and efficient approach to apply these solvents to adhesives. In particular, the disclosure provides a package assembly or kit to hold and apply an adhesive removing device conveniently, inexpensively and effectively.

In embodiments, the enclosure optionally includes a compartment configured and dimensioned for housing applicators. At least one applicator is contained within the enclosure. In some embodiments, the applicator includes a shaft having two ends and an absorbent portion at one or each end of the shaft. The two absorbent portions may be differently configured for wiping and drying a surface to be treated, and for applying compositions, respectively.

In another embodiment, the applicators contained within the enclosure comprise at least one absorbent portion on a distal end and on a proximal end of an elongated shaft of the applicator wherein each absorbent portion is individually wrapped with a removable plastic layer.

In embodiments, the enclosure includes a base portion and a top layer. The base portion comprises a fibrous layer while the top layer comprises a plastic layer. The fibrous layer comprises polyolefin, cellulosic, alginic and polysaccharide fibers while the plastic layer comprises polyethylene.

In embodiments, the composition material can be sequentially sterilized—e.g., once before being placed on the applicator, after being placed in the enclosure, and optionally after the applicator is placed in the enclosure. In such embodiments, the composition material can be subjected to sequential sterilization procedures with substantially no effect on the effectiveness of the solvent occurring.

In further embodiments, a method for storing and applying an adhesive remover in accordance with the embodiments above are disclosed.

BRIEF DESCRIPTION OF THE DRAWINGS

Although specific embodiments of the present disclosure will now be described with reference to the drawings, it should be understood that such embodiments are by way of example only and merely illustrative of but a small number of the many possible specific embodiments which can represent applications of the principles of the present disclosure. Various changes and modifications obvious to one skilled in the art to which the present disclosure pertains are deemed to be within the spirit, scope and contemplation of the present disclosure as further defined in the appended claims.

DETAILED DESCRIPTION

In general, the present disclosure is directed to an adhesive removing device and package assembly or kit which includes, a wiping mechanism with a biocompatible solvent composition embedded in an absorbent portion of the wiping mechanism therein. The package assembly according to the present disclosure can be used in conjunction with a wide variety of applications of biocompatible solvent composition materials, wherein it is necessary or desirable to efficiently and easily remove an adhesive material. Examples include, but are not limited to, those applicable to medical, industrial, and home use. For example, the package assembly in accordance with the present disclosure may be used to apply a composition of solvent and moisturizing agent, for the removal of wound closure adhesives such as those used for surgically incised or traumatically lacerated tissues; retarding blood flow from wounds; dressing burns; dressing skin or treating stomatitis or other superficial or surface sores or wounds.

The package assembly may be used to store and apply a wide variety of solvents, including but not limited to: isopropyl alcohol, benzyl alcohol, esters of acetic acid and/or mixtures thereof. The package assembly may be used on a number of different adhesives including polymerizable liquid adhesives such as 1,1-disubstituted ethylene monomers and polymers, including cyanoacrylate monomers such as the alpha-cyanoacrylates.

One particular application of the package assembly of the present disclosure is in conjunction with the storage and application of a composition comprising a solvent material and a moisturizing agent for medical or surgical procedures. It should be appreciated that any known or later developed solvent for removing adhesive materials or any later developed moisturizing agents can be used in conjunction with this disclosure.

The presently disclosed adhesive removing device and kit will be further described in conjunction with the accompanying figures showing exemplary embodiments of the present disclosure. In the figures, like numerals have been used to identify like components.

Figure 1:
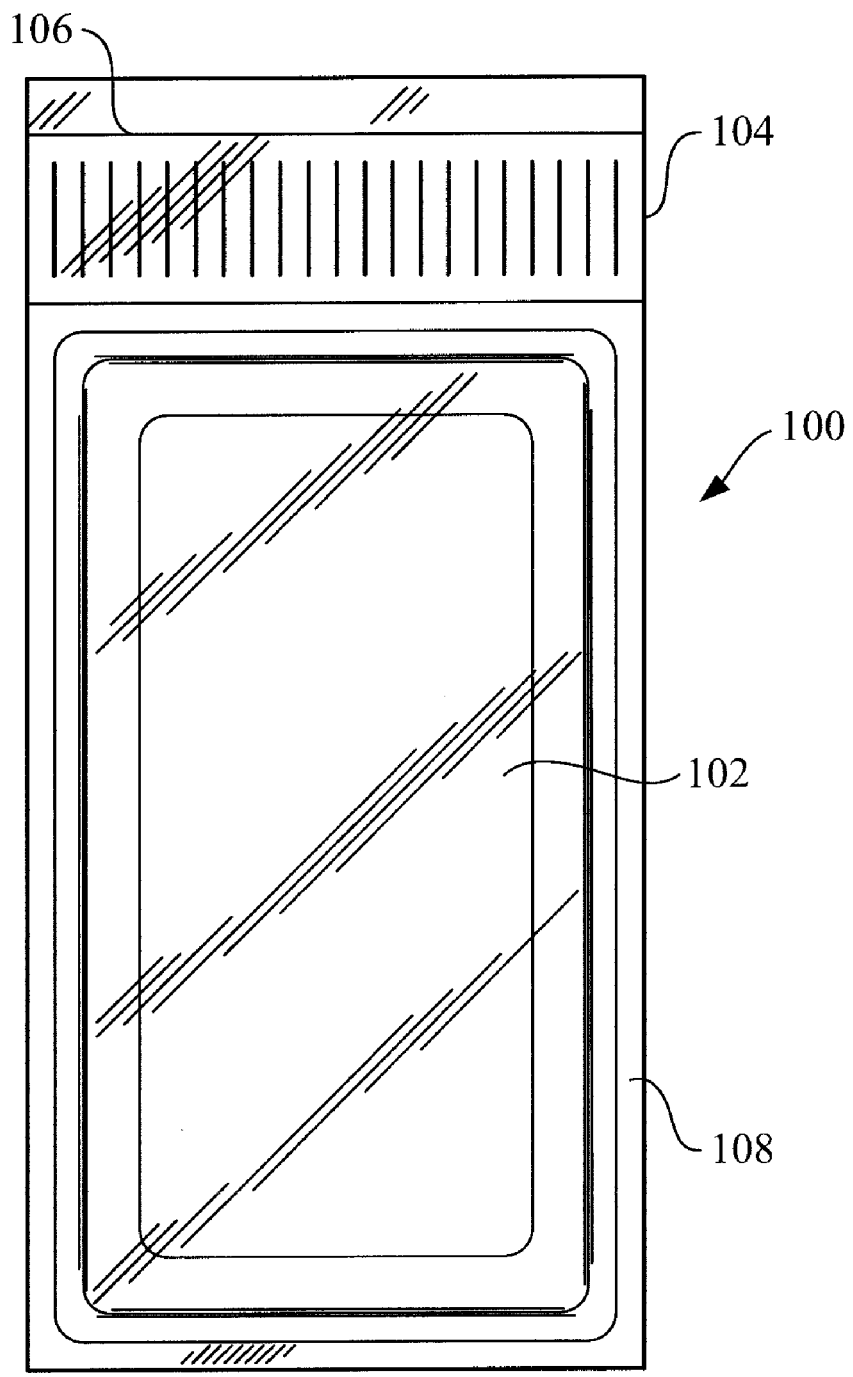
FIG. 1 is a top plan view of an enclosure of the package assembly or kit in accordance with the embodiments of the present disclosure.

FIG. 1 shows an enclosure 100 of a package assembly or kit in accordance with an embodiment of the present disclosure to hold and apply an adhesive removing device conveniently, inexpensively and effectively. The enclosure 100 contains a base portion 104 and a top layer 108 sealed along the edges and having one peelable flap 106 along one edge wherein the user may easily remove the top layer from the base portion. The enclosure 100 may include a cavity or compartment 102 which is configured and dimensioned to hold at least one applicator 210 (see FIG. 2). The enclosure 100 may be any of a variety of shapes and designs dependent on numerous factors including, for example, the specific contents of the enclosure and the intended use of the adhesive removing device contained within the enclosure.

Figure 2:
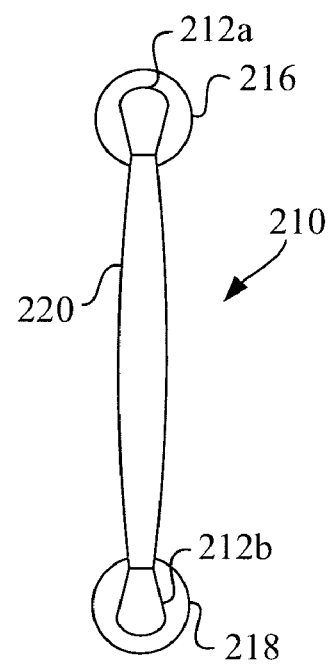
FIG. 2 is a perspective view showing an applicator in accordance with the embodiments of the present disclosure.

Referring to FIG. 2, the applicator 210 includes at least one absorbent portion 212a at a distal end of an elongated shaft 220 and at least one absorbent portion 212b on a proximal end of elongated shaft 220.

The applicator 210 may be formed of any of a wide variety of materials including but not limited to polymerized materials such as plastics, foams, rubbers, thermoplastics, thermosets, metals, for example, or any other suitable material. Further, it should be recognized that the applicator according to the other embodiments of the present disclosure, as described herein, may also be constructed of hydrophilic polyurethane foam. In general, the only limitation on the materials used to fabricate them is that the material must be sufficiently compatible with the composition to be dispensed therein that undesirable effects on the composition do not occur during contact of the composition with the enclosure 100.

The absorbent portion 212 may be constructed of any suitable hydrophilic material such as a cotton swab or fibrous pad material, for example. The material, such as cotton, forming the absorbent portion 212 of the applicator 210 can absorb a composition, such as various solvent compositions. The absorbed composition can then be applied to a surface, such as a wound closure adhesive.

In one embodiment, an applicator 210 may have at least one absorbent portion 212a or 212b with a composition embedded therein and further wrapped with a layer of polymeric material 216 or 218. The polymeric material layer 216 or 218 increases the effectiveness of sterility of the applicator as well as eliminates the chances of altering the opposite absorbent portion's function.

Furthermore, the material layer can be formed of polymeric materials that have been modified by a post-halogenation treatment to be highly resistant to attack, solvation and/or permeation and thus provide an extended shelf life of the containers and biocompatible compositions.

Figure 3:
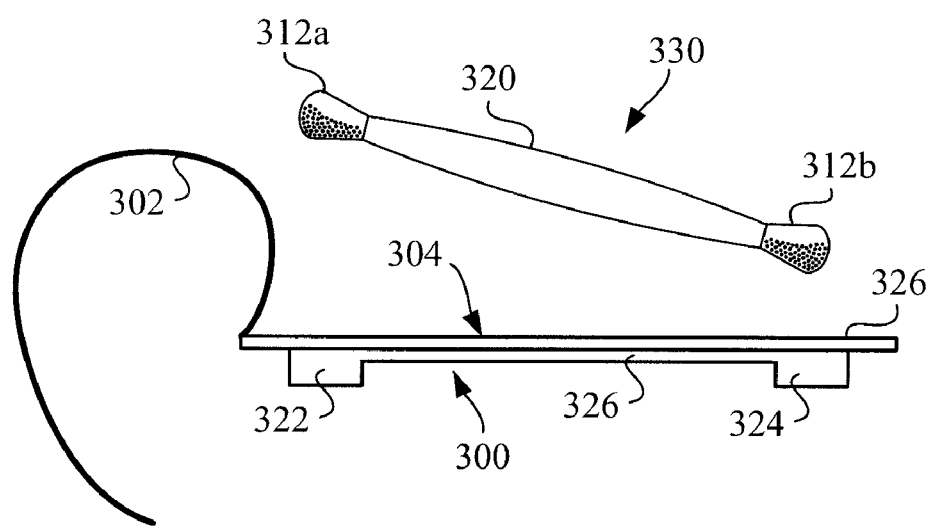
FIG. 3 is a side elevation view of an enclosure and applicator in accordance with the embodiments of the present disclosure.

Now referring to FIG. 3, an applicator 330 is illustrated removed from enclosure 300 in accordance with embodiments of the present disclosure. The applicator 330 includes a first absorbent end 312a and a second absorbent end 312b. The absorbent end 312a in FIG. 3 is tapered such that the tip of the absorbent end 312a is wider in dimension than the base. The dimensions of the applicator 330 allow the applicator to be used to apply adhesive remover in a variety of environments and spatial constraints. The wider end of the applicator in the embodiment of FIG. 3 is useful when the surface to be treated needs to be dried after the solvent composition is applied to the adhesive and dissolves the adhesive.

However, it should be recognized that the applicator 330 shown in FIG. 3 is only illustrative and not limiting. For example, the applicator may include only one absorbent end. Further, the absorbent end or ends of the applicator may be a wide variety of shapes and sizes such as circular, elliptical, elongated, curved or square depending on the particular area where the adhesive needs to be removed. Also, in alternative illustrative embodiments, the absorbent end could be in the form of a brush, sponge or constructed of foam.

Still referring to FIG. 3, enclosure 300 includes a base portion 304 and a top layer 302. The top layer 302 may be removably attached to the base 304. However, it should be recognized that in accordance with the present disclosure the interrelationship of the base 304 and the top layer 302 is not limited to the arrangement shown in FIG. 3., but rather may be a wide variety of shapes and designs.

When a user wants to apply the adhesive removing device to an adhesive wound closure, for example, the user opens the enclosure 300 via the peelable flap 302 and removes an applicator 330 from the enclosure 300. Then, the absorbent portion 312a or 312b is used to make physical contact with the surface upon which the adhesive is to be removed.

It will be understood that a UV stabilizing agent may be included in any of the enclosures for applicators described herein to provide the UV stabilization and protection functions to the enclosures and protect the materials of the applicators from degradation due to exposure to UV radiation.

The enclosure 300, can be any conventional enclosure or pouch used for medical devices manufactured from any suitable material known to those skilled in the art. In one illustrative embodiment, enclosure 300 is formed by heat sealing two panels of aluminum foil coated on the interior surfaces thereof with a heat sealable polymeric composition. Other means for sealing the enclosure may be employed as are well known to those skilled in the art.

In another embodiment, enclosure 300 may be formed from a hydrophobic material. The term "hydrophobic", as described herein, refers to materials that are not normally water soluble and absorb relatively low amounts of water, i.e., less than about 10% by weight. Some examples of these materials include, but are not limited to, polymers, copolymers, homopolymers, and block copolymers formed from monomers such as ε-caprolactone, glycolide, 1-lactide, d,1-lactide, d-lactide, meso-lactide, trimethylene carbonate, 4,4-dimethyl-1,3-dioxan-2-one, p-dioxanone, dioxepanone, δ-valerolactone, β-butyrolactone, ε-decalactone, 2,5-diketomorpholine, pivalolactone, α,α-diethylpropiolactone, 6,8-dioxabicyclooctan-7-one, ethylene carbonate, ethylene oxalate, 3-methyl-1,4-dioxane-2,5-dione, 3,3-dimethyl-1,4-dioxane-2,5-dione, and other substituted glycolides, and substituted lactides. Some additionally useful hydrophobic materials include polyolefins (i.e. Tyvek.®) and polysiloxanes.

In another embodiment, enclosure 300 may be formed from a hydrophilic material. The term "hydrophilic", as described herein, refers to materials that are normally water soluble and absorb relatively high amounts of water. Some examples of these materials include, but are not limited to, polyalkylene glycols, such as polyethylene glycol, polyacrylates such as polymers of methacrylates and 2-hydroxyethyl methacrylate, aminoalkyl acrylates, such as N,N-dimethylacrylamide, polyvinylalcohols, polyvinylpyrrolidones, polyoxyethylenes, polyacrylamides, poly(2-hydroxy-ethyl-methacrylate), polymethacrylamide, dextran, alginic acid, sodium alginate, polysaccharides, gelatine and copolymers of two or more of the monomers from which the above polymers are derived and polyoxyethylene/polyoxypropylene block copolymers.

In still another embodiment, enclosure 300 can be made of a combination of hydrophobic and hydrophilic materials. An example of an enclosure with a combination of hydrophobic and hydrophilic materials can include a polyolefin sheet (i.e. Tyvek.®) and a polyethylene sheet adhered together with a release agent.

The base 304 is elongated and includes at least one cavity 322 or 324 formed within. Specifically, the base 304 includes a cavity for at least one applicator 330. The applicator cavity 326 is formed in the shape of an elongated slot and extends along the length of the base 304. However, the present disclosure is not limited to one applicator cavity 326. For example, a single cavity might be provided, in which a plurality of applicators are positioned side by side for additional uses. In alternative embodiments, a plurality of applicators may be positioned in a single enclosure or may be disposed individually in separate enclosures.

Alternatively or in addition, the adhesive removing composition may contain preservatives and/or stabilizers to counteract effects of minor amounts of such contaminants.

The adhesive removing composition includes a suitable solvent for removing adhesive from the surface of skin and/or wound closure. Suitable solvents include but are not limited to, glycols, such as ethylene glycol, propylene glycol, diethylene glycol, dipropylene glycol, polyethylene glycol, and polypropylene glycol; glycol ethers; alcohols, such as methanol, ethanol, propanol, phenethyl alcohol and phenoxypropanol; ketones, such as acetone and methyl ethyl ketone; esters, such as ethyl acetate, butyl acetate, triacetyl citrate, and glycerol triacetate; carbonates, such as propylene carbonate and dimethyl carbonate; and mixtures thereof. It is preferred that the solvent is selected from water, glycols, glycol ethers, esters and mixtures thereof.

The adhesive removing composition may also contain suitable bioactive materials which include, but are not limited to, medicaments such as antibiotics, antimicrobials, antiseptics, bacteriocins, bacteriostats, disinfectants, steroids, anesthetics, fungicides, anti-inflammatory agents, antibacterial agents, antiviral agents, antitumor agents, growth promoting substances, moisturizing components, antioxidants, tackifiers, solubilizers, colorants, perfumes, surfactants, UV absorbers, inorganic fillers and pH adjusting agents or mixtures thereof.

Preferable medicaments are those that are anions or help in radical generation or that are ion pairs or are themselves radicals. In embodiments, the medicament includes, but is not limited to a quaternary ammonium halide such as alkylbenzyldimethylammonium chloride (benzalkonium chloride; BAC) with an alkyl containing 6-18 carbon atoms, its pure components, or mixtures thereof, or benzethonium chloride; or a salt of sulfadiazine, such as a silver, sodium, or zinc salt, water-soluble placenta extract, allantoin, lecithin, amino acids, kojic acid, proteins, saccharides, hormones, placenta extract, components extracted from various types of herbal medicine such as aloe, sponge gourd and liquorice, vitamin A, vitamin C, vitamin D, vitamin E and other vitamins, etc. or mixtures thereof.

With regard to the moisturizing components, an aqueous solution of succinylkefiran, an aqueous solution of acetylkefiran, an aqueous solution of maleylkefiran, malt sprout extract, Rosae fructus extract, orange extract, orange fruit juice, raspberry extract, kiwi extract, cucumber extract, gardenia extract, grapefruit extract, *Crataegus cuneata* extract, *xanthoxylum* extract, *Crataegus oxycantha* extract, *Juniperus communis* extract, *Zizyphi* fructus extract, *Ziziphus jujuba* extract, duke extract, tomato extract, grape extract, sponge gourd extract, lime fruit juice, apple extract, apple fruit juice, lemon extract, lemon fruit juice, etc. can be added singly or in combinations of two or more types.

With regard to the antioxidants, ascorbic acid, propyl gallate, butyl hydroxyanisole, dibutyl hydroxytoluene, nordihydroguairetic acid, tocopherol, tocopherol acetate, etc. or mixtures thereof can be added.

With regard to the tackifiers, casein, pullulan, agar, dextran, sodium alginate, soluble starch, carboxy starch, dextrin, carboxymethyl cellulose, sodium carboxymethyl cellulose, methyl cellulose, ethyl cellulose, hydroxyethyl cellulose, polyvinyl alcohol, polyethylene oxide, polyacrylamide, polyacrylic acid, polyvinylpyrrolidone, carboxyvinyl polymer, polyvinyl ether, methyl vinyl ether-maleic anhydride copolymer, isobutylene-maleic anhydride copolymer, polyethyleneimine, etc. can be added.

With regard to the solubilizers, benzyl alcohol, pyrrothiodecane, peppermint oil, isopropyl myristate, crotamiton, etc. or mixtures thereof can be added.

With regard to the colorants, those that can have a large influence on the image of the preparation and contribute to an improvement in the user's feeling during use and a feeling of skin revitalization are preferred, for example, approved colorants such as Red No. 2 (amaranth), Red No. 3 (erythrosine), Red No. 102 (new coccine), Red No. 104 (1) (phloxine B), Red No. 105 (1) (rose bengal), Red No. 106 (acid red), Yellow No. 4 (tartrazine), Yellow No. 5 (sunset yellow FCF), Green No. 3 (fast green FCF), Blue No. 1 (brilliant blue FCF) and Blue No. 2 (indigo carmine) or mixtures thereof can be added, but they are not particularly limited thereby.

With regard to the surfactants, anionic surfactants such as sodium dioctylsulfosuccinate, alkylsulfate salts, 2-ethylhexylalkylsulfate ester sodium salt and sodium n-dodecylbenzenesulfonate, cationic surfactants such as hexadecyltrimethylammonium chloride, octadecyldimethylbenzylammonium chloride and polyoxyethylenedodecylmonomethylammonium chloride, nonionic surfactants such as polyoxyethylene stearyl ether, polyoxyethylene tridecyl ether, polyoxyethylene nonyl phenyl ether, polyoxyethylene octyl phenyl ether, polyoxyethylene monostearate, sorbitan monostearate, sorbitan monopalmitate, sorbitan sesquioleate, polyoxyethylene sorbitan monolaurate, polyoxyethylene sorbitan monooleate, glycerol monostearate, polyglycerol fatty acid esters and polyoxyethylene octadecylamine can be added.

With regard to the UV absorbers, p-aminobenzoic acid, p-aminobenzoate esters, amyl p-dimethylaminobenzoate, salicylate esters, menthyl anthranilate, umbelliferone, esculin, benzyl cinnamate, cinoxate, guaiazulene, urocanic acid, 2-(2-hydroxy-5-methylphenyl)benzotriazole, 4-methoxybenzophenone, 2-hydroxy-4-methoxybenzophenone, dioxybenzone, octabenzone, dihydroxydimethoxybenzophenone, sulisobenzone, benzoresorcinol, octyldimethyl p-aminobenzoate, ethylhexyl p-methoxy cinnamate, etc. or mixtures thereof can be added.

With regard to the inorganic fillers, titanium oxide, talc, zinc oxide, hydrated silica, magnesium carbonate, calcium hydrogenphosphate, magnesium silicate, diatomaceous earth, silicic anhydride, bentonite, etc. or mixtures thereof can be added.

With regard to the pH adjusting agents, acetic acid, formic acid, lactic acid, tartaric acid, oxalic acid, benzoic acid, glycolic acid, malic acid, citric acid, hydrochloric acid, nitric acid, sulfuric acid, sodium hydroxide, potassium hydroxide, methylamine, ethylamine, propylamine, dimethylamine, diethylamine, dipropylamine, trimethylamine, triethylamine, tripropylamine, monoethanolamine, monoethanolamine, monopropanolamine, dimethanolamine, diethanolamine, dipropanolamine, trimethanolamine, triethanolamine, tripropanolamine, etc., or mixtures thereof can be added.

Another optional ingredient is selected from essential fatty acids (EFAs), i.e., those fatty acids which are essential for the plasma membrane formation of all cells, in keratinocytes EFA deficiency makes cells hyperproliferative. Supplementation of EFA corrects this. EFAs also enhance lipid biosynthesis of epidermis and provide lipids for the barrier formation of the epidermis. The essential fatty acids are preferably chosen from linoleic acid, Y-linolenic acid, homo-Y-linolenic acid, columbinic acid, eicosa-(n-6,9,13)-trienoic acid, arachidonic acid, Y-linolenic acid, timnodonic acid, hexanoic acid and mixtures thereof.

Antimicrobial and antifungal actives can be effective to prevent the proliferation and growth of bacteria and fungi. Non-limiting examples of antimicrobial and antifungal actives include antibiotic drugs, quaternary ammonium compounds such as benzalkonium chloride; benzethonium chloride; triclosan; triclocarban; and mixtures thereof and the like. Anti-wrinkle, anti-skin atrophy and skin repair actives can be effective in replenishing or rejuvenating the epidermal layer. These actives generally provide these desirable skin care benefits by promoting or maintaining the natural process of desquamation. Non-limiting examples of anti-wrinkle and anti-skin atrophy actives include retinoic acid and its derivatives, and the like. Skin barrier repair actives are those skin care actives which can help repair and replenish the natural moisture barrier function of the epidermis. Non-steroidal cosmetic soothing actives can be effective in preventing or treating inflammation of the skin. The soothing active enhances the skin appearance benefits of the present disclosure, e.g., such agents contribute to a more uniform and acceptable skin tone or color. Benefit agents in the present disclosure may also include anti-itch ingredients. Suitable examples of anti-itch ingredients which are useful in the compositions of the present disclosure include hydrocortisone, and the like.

The adhesive removing solution of the present disclosure is formulated with the above described components of solvent and moisturizing agents as the essential ingredients. The contents of the moisturizing agent component in the remover solution should be in the ranges from 0.01% to 10% by weight and from 0.1% to 30% by weight, respectively, or, preferably, in the ranges from 0.1% to 5% by weight and from 0.5% to 10% by weight, respectively, the balance to 100% by weight being the solvent component and optionally, water.

According to this disclosure, in some embodiments, the adhesive removing composition and other components of the package assembly or kit may be sterilized. For example, the enclosure containing the applicator 330 containing the adhesive removing composition embedded therein shown in FIG. 3 may be sterilized. The enclosure 300 may be sterilized by the same or a different method as that used for the adhesive removing composition or applicator 330. Also, the enclosure 100, illustrated in FIG. 1, may be sterilized together with the applicator 210 enclosed therein.

Various sterilization processes may be used for the separate components of the package assembly or kit. Examples include, but are not limited to, chemical sterilization (e.g., exposure to ethylene oxide or hydrogen peroxide vapor), physical sterilization (e.g., dry or moist heat) or other techniques such as microwave irradiation, gamma radiation, ionizing radiation, and electron beam irradiation. It will be understood that the same or different sterilization technique may be used to sterilize different components of the package assembly.

However, in embodiments in which the enclosure 100 is formed of a non-air permeable material such as a plastics material, the enclosure may also be sterilized. Further, in some embodiments, a non-air permeable material, such as a plastics material, may be applied over an air permeable material such as a paper material. For example, a plastics material may be applied to a cardboard enclosure by a shrink wrapping process. In such embodiments, after applying the plastics material or the like over the enclosure, the package assembly may be sterilized.

According to illustrative embodiments of the present disclosure, sequential sterilization can be performed with substantially no resulting change to the adhesive removing composition. Accordingly, the sterilized adhesive compositions can have a satisfactory shelf life.

While the present disclosure presents specific embodiments outlined above, it is evident that many alternatives, modifications and variations may be apparent to those skilled in the art. For example, various different combinations, and shapes, sizes and arrangements, of the described features are contemplated. Accordingly, the embodiments of the present disclosure as set forth herein are intended to be illustrative, not limiting. Various changes may be made without departing from the spirit and scope of the present disclosure.

We claim:

1. A kit for storing and applying an adhesive removing device, comprising:
   an enclosure including a base portion and a removable top layer releasably secured thereto;
   an adhesive removing device including:
   at least one wiping mechanism within said enclosure wherein the wiping mechanism includes at least one absorbent portion on a distal end and proximal end of an elongated shaft;
   a biocompatible composition including a solvent and a moisturizing agent embedded in said at least one absorbent portion of said wiping mechanism wherein the adhesive removing device is removably disposed in the enclosure; and
   at least one removable layer configured and dimensioned to wrap around said at least one absorbent portion.

2. The kit for storing and applying an adhesive removing device as in claim 1, wherein the entire contents of the enclosure are sterilized.

3. The kit for storing and applying an adhesive removing device as in claim 1, wherein the base portion and top layer of the enclosure includes top and bottom transverse edges and longitudinal side edges adhered together and at least one peelable flap on a top edge for permitting access to the wiping mechanism.

4. The kit for storing and applying an adhesive removing device as in claim 1, wherein the enclosure is made from a material selected from the group consisting of hydrophobic materials, hydrophilic materials and combinations thereof.

5. The kit for storing and applying an adhesive removing device as in claim 1, wherein the base portion comprises a fibrous layer and said top layer comprises a plastic layer.

6. The kit for storing and applying an adhesive removing device as in claim 5, wherein the fibrous layer comprises polyolefin fibers.

7. The kit for storing and applying an adhesive removing device as in claim 5, wherein the fibrous layer comprises cellulosic fibers.

8. The kit for storing and applying an adhesive removing device as in claim 5, wherein the fibrous layer comprises alginic fibers.

9. The kit for storing and applying an adhesive removing device as in claim 5, wherein the fibrous layer comprises polysaccharide fibers.

10. The kit for storing and applying an adhesive removing device as in claim 5, wherein the plastic layer is polyethylene.

11. The kit for storing and applying an adhesive removing device as in claim 1, wherein the removable top layer releasably secured to the base portion includes a release agent to facilitate separation of said plastic layer from said fibrous layer to open said enclosure.

12. The kit for storing and applying an adhesive removing device as in claim 11, wherein the release agent comprises an adhesive.

13. The kit for storing and applying an adhesive removing device as in claim 1, wherein the wiping mechanism is selected from a group consisting of cloth wipes, fibrous pad, surface swab applicators and sponges.

14. The kit for storing and applying an adhesive removing device as in claim 1, wherein the solvent is selected from the group consisting of: glycols, such as ethylene glycol, propylene glycol, diethylene glycol, dipropylene glycol, polyethylene glycol, polypropylene glycol; glycol ethers; alcohols, such as methanol, ethanol, propanol, phenethyl alcohol, phenoxypropanol; ketones, such as acetone, methyl ethyl ketone; esters, such as ethyl acetate, butyl acetate, triacetyl citrate, glycerol triacetate; carbonates, such as propylene carbonate, dimethyl carbonate; and/or mixtures thereof.

15. The kit for storing and applying a wound closure adhesive removing device as in claim 1, wherein the moisturizing agent is selected from the group consisting of: an aqueous solution of succinylkefiran, an aqueous solution of acetylkefiran, an aqueous solution of maleylkefiran, malt sprout extract, Rosae fructus extract, orange extract, orange fruit juice raspberry extract, kiwi extract, cucumber extract, gardenia extract, grapefruit extract, *Crataegus cuneata* extract, *xanthoxylum* extract, *Crataegus oxycantha* extract, *Juniperus communis* extract, *Zizyphi* fructus extract, *Ziziphus jujuba* extract, duke extract, tomato extract, grape extract, sponge gourd extract, lime fruit juice, apple extract, apple fruit juice, lemon extract, lemon fruit juice, aloe and/or mixtures thereof.

16. The kit for storing and applying an adhesive removing device as in claim 1, wherein the solvent is ethanol.

17. The kit for storing and applying a wound closure adhesive removing device as in claim 1, wherein the moisturizing agent is aloe.

18. The kit for storing and applying an adhesive removing device as in claim 1, wherein the removable layer is made from a material selected from the group consisting of hydrophobic materials, hydrophilic materials and combinations thereof.

19. The kit for storing and applying an adhesive removing device as in claim 1, wherein the removable layer is made of polyethylene.

20. The kit for storing and applying an adhesive removing device as in claim 1, wherein the enclosure includes at least one compartment configured and dimensioned for housing at least one adhesive removing device.

21. The kit for storing and applying an adhesive removing device as in claim 1, wherein the base portion includes at least one cavity for housing the at least one absorbent portion.

22. The kit for storing and applying an adhesive removing device as in claim 1, wherein the base portion includes at least one cavity formed in the shape of an elongated slot and extends along the length of the base.

* * * * *